United States Patent [19]
Tsuzuki et al.

[11] Patent Number: 4,560,762
[45] Date of Patent: Dec. 24, 1985

[54] 2-ALKYLAMINOPYRIDINE DERIVATIVES

[75] Inventors: Kenji Tsuzuki, Shinnanyo; Hideo Morinaka, Utsunomiya, both of Japan

[73] Assignee: Toyo Soda Manufacturing Co. Ltd., Shinnanyo, Japan

[21] Appl. No.: 497,408

[22] Filed: May 23, 1983

[30] Foreign Application Priority Data

| May 27, 1982 | [JP] | Japan | 57-88828 |
| May 27, 1982 | [JP] | Japan | 57-88829 |
| Jul. 7, 1982 | [JP] | Japan | 57-116888 |
| Jul. 9, 1982 | [JP] | Japan | 57-118619 |
| Jul. 9, 1982 | [JP] | Japan | 57-118620 |
| Apr. 28, 1983 | [JP] | Japan | 58-73857 |

[51] Int. Cl.$^4$ .................. C07D 213/74; C07D 213/64
[52] U.S. Cl. ........................ 546/297; 546/304; 546/292; 71/94
[58] Field of Search ................ 546/297, 304

[56] References Cited

U.S. PATENT DOCUMENTS 3,450,707  6/1969  Bailey .................... 546/304
3,826,643  7/1974  Diehl et al. ................ 71/94
3,948,910  4/1976  Johnston et al. ........... 260/239.75

OTHER PUBLICATIONS

March, Advanced Organic Chemistry, Reactions, Machanisms and Structure Second Edition, pp. 357–358, McGraw–Hill Pub.
Journal of the American Chemical Society, vol. 71, pp. 340–342, 1949; vol. 46, pp. 1460–1470, 1924.
Rec. Trav. Chem, vol. 55, pp. 122–130, 1936.

*Primary Examiner*—Alan L. Rotman
*Attorney, Agent, or Firm*—Oblon, Fisher, Spivak, McClelland & Maier

[57] ABSTRACT

2-Alkylaminopyridine derivatives represented by a general formula of

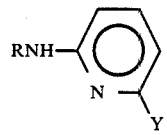

wherein R denotes a lower alkyl group and Y denotes a methoxy group or a halogen atom, and method for producing the same.

5 Claims, No Drawings

2-ALKYLAMINOPYRIDINE DERIVATIVES

DETAILED DESCRIPTION OF THE INVENTION

This invention relates to 2-alkylaminopyridine derivatives represented by a general formula of

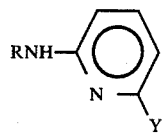

wherein R denotes a lower alkyl group such as methyl, ethyl, n-propyl or isopropyl group and Y denotes a methoxy group or a halogen atom, and methods for producing the same. The above 2-alkylaminopyridine derivatives of this invention are novel compounds and are useful as intermediates to some substances which can be used for medicines, agricultural chemicals and the like.

2-Methoxy-6-methylaminopyridine, one of the compounds of this invention, is reacted with O-2-naphthyl chlorothioformate to give O-2-naphthyl N-(6-methoxy-2-pyridyl)-N-methylthiocarbamate. Also 2-ethylamino-6-methoxypyridine, another compound of this invention, is reacted with O-4-isopropylphenyl chlorothioformate to give O-4-isopropylphenyl N-ethyl-N-(6-methoxy-2-pyridyl)thiocarbamate. These obtained O-2-naphthyl N-(6-methoxy-2-pyridyl)-N-methylthiocarbamate and O-4-isopropylphenyl N-ethyl-N-(6-methoxy-2-pyridyl)thiocarbamate can be prepared to herbicides including the same as an effective ingredient, respectively. These compounds are preferable as herbicides for use in paddy fields, because they show extremely excellent herbicidal activity against miscellaneous weeds including barnyard grass as typical one and are harmless to transplanted rice plants at the same time. Furthermore, they show excellent herbicidal selectivity between weeds belonging to gramineous weed and broadleaved crops in the treatment for farmland soil, and therefore they have applicability in herbicides used in farmlands.

The 2-alkylaminopyridine derivatives of this invention can be produced by the following reactions (A), (B) or (C). Equation of reaction (A)

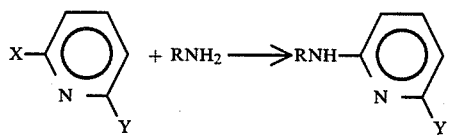

wherein R and Y denote the same as above-mentioned respectively, and X denotes a chlorine atom or a bromine atom. Equation of reaction (B)

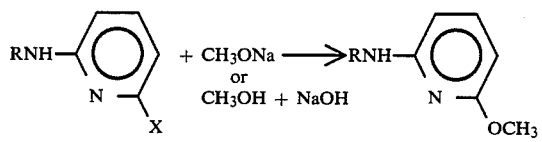

wherein R and X denote the same as above respectively. Equation of reaction (C)

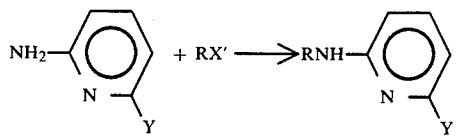

wherein R and Y mean the same as above, and X' denote a halogen atom.

The equation of reaction (A) is explained by exemplifying a method of reacting 2-halo-6-methoxypyridine with alkylamine. In this method, used amount of alkylamine is 2 to 10 times moles of 2-halo-6-methoxypyridine, and a solvent is employed in order to make this reaction proceed smoothly.

As the solvent, water, alcohol, aromatic hydrocarbon such as benzene, aliphatic ether such as diethyleneglycoldimethylether, or cyclic ether such as dioxane, which are non-reactive with 2-halo-6-methoxypyridine and furthermore dissolves alkylamine, can be exemplified.

Temperature of the reaction is about 100° C. to about 250° C., preferably about 140° C. to 200° C., and the reaction can be completed within 20 hours. Further, this reaction proceed more preferably in the presence of copper or copper compound of inorganic salt such as copper sulfate, copper chloride, copper nitrate and the like, of organic metal salt such as copper naphthenate, copper acetate and the like, of metal oxide such as cupric oxide etc., or of metal hydroxide such as copper hydroxide.

The equation of reaction (B) is explained by exemplifying a method of reacting 2-alkylamino-6-halopyridine with methanol in the presence of alkaline metal hydroxide. In this method, as the alkaline metal hydroxide, lithium hydroxide, sodium hydroxide, potassium hydroxide and the like are exemplified. The alkaline metal hydroxide is used in amount of not less than 1 times mole, preferably about 2 to 4 times moles to 2-alkylamino-6-halopyridine.

Reaction temperature thereof is usually about 100° C. to about 220° C., preferably about 140° C. to about 200° C. Reaction time thereof may be varied by reaction temperature, used amount of alkaline metal hydroxide and other conditions, but the reaction can be completed within 20 hours.

2-Alkylamino-6-halopyridine, which is a starting material thereof, can be produced by a reaction of 2,6-dihalopyridine with alkylamine.

This invention is detailed by examples, but this invention is not restricted within these examples.

EXAMPLE 1

Into an autoclave of 200 ml volume equipped with electromagnetic stirrer, 43 g of 2-chloro-6-methoxypyridine and 75 ml of 40% conc. methylamine aqueous solution were charged and were subjected to reacting each other at 180° C. for 12 hours.

After completion of the reaction, the autoclave was cooled and opened to take out the reaction mixture. Then, after adding 30 g of solid sodium hydroxide to the reaction mixture, the mixture was subjected to extraction with ether. The ether solution of the extract was dried over solid sodium hydroxide, and ether was distilled off. The residue was subjected to vacuum distillation to give 18 g of 2-methoxy-6-methylaminopyridine of b.p. 88°–92° C./5 mmHg.

Infrared absorption spectrum (NaCl) 3420 (—NH), 2950 (C—H), 1600, 1475, 1420

( 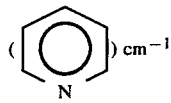 ) cm$^{-1}$

Nuclear magnetic reasonance absorption spectrum (CCl$_4$, internal standard TMS)

| δ | 2.86 (d) ppm | (3H) |
| δ | 3.85 (S) ppm | (3H) |
| δ | 4.40 (bS) ppm | (1H) |
| δ | 5.84 (d) ppm | (1H) |
| δ | 5.94 (d) ppm | (1H) |
| δ | 7.12 (t) ppm | (1H) |

A result of elemementary analysis (as C$_7$H$_{10}$N$_2$O) was as follows.

|  | C | H | N | O |
|---|---|---|---|---|
| Found (%) | 60.75 | 7.22 | 20.35 | 11.68 |
| Calculated (%) | 60.85 | 7.30 | 20.27 | 11.58 |

Molecular weight by GC-MS 138

EXAMPLE 2

In the same reaction apparatus as in Example 1, 30 g of 2-bromo-6-methoxypyridine and 75 ml of 40% conc. methylamine aqueous solution were subjected to reacting each other at 140° C. for 18 hours.

After completion of the reaction, the similar experimental procedure as in Example 1 was carried out to give 11 g of 2-methoxy-6-methylaminopyridine.

EXAMPLE 3

In the same reaction apparatus as in Example 1, 25 g of 2,6-dichloropyridine and 60 ml of 40% conc. methylamine aqueous solution were charged and were subjected to reacting each other at 120° C. for 5 hours.

After completion of the reaction, the autoclave was cooled and the contents thereof was taken out, and then solid was collected through filtration.

Then, this solid was recrystallized from n-hexane to give 22.7 g of 2-chloro-6-methylaminopyridine of m.p. 63.5°–64.5° C.

Then, in the same reaction apparatus as in Example 1, 20 g of 2-chloro-6-methylaminopyridine, 11.5 g of sodium hydroxide and 80 ml of methanol were charged, and they were subjected to reacting each other at 170° C. for 5 hours.

After completion of the reaction, the autoclave was cooled and the contents thereof were taken out, and solid was removed by filtration. Then, methanol was distilled out of the filtrate and, after adding water to the residue, it was subjected to extraction with ether. The ether solution of the extract was dried over anhydrous magnesium sulfate and, after distilling out ether, the residue was subjected to vacuum distillation to give 15.6 g of 2-methoxy-6-methylaminopyridine of b.p. 88°–92° C./5 mmHg.

Yield of 2-methoxy-6-methylaminopyridine was 80.5%, calculated from the base of 2-chloro-6-methylaminopyridine.

EXAMPLE 4

In the same reaction apparatus as in Example 1, 20 g of 2-bromo-6-methylaminopyridine, 18 g of potassium hydroxide and 80 ml of methanol were charged and they were subjected to reacting each other at 160° C. for 4 hours.

Thereafter, the reaction mixture was treated in the similar manner as in Example 1 to give 12.0 g of 2-methoxy-6-methylaminopyridine.

Yield of 2-methoxy-6-methylaminopyridine was 81.3%, calculated from the based of 2-bromo-6-methylaminopyridine.

EXAMPLE 5

In the same reacting apparatus as in Example 1, 20 g of 2-chloro-6-ethylaminopyridine, 60 ml of methanol and 12 g of sodium hydroxide were charged and they were subjected to reacting each other at 170° C. for 5 hours.

After completion of the reaction, the similar experimental procedure as in Example 3 was carried out, and the reacting product was distilled under reduced pressure to give 13.9 g of 2-ethylamino-6-methoxypyridine of b.p. 125°–127° C./20 mmHg.

Infrared absorption spectrum (NaCl) 3420 (—NH), 2960 (C—H), 1600, 1460, 1420

( 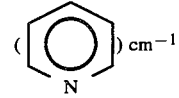 ) cm$^{-1}$

Nuclear magnetic reasonance absorption spectrum (CDCl$_3$, internal standard TMS)

| δ | 1.10 (t) ppm | (3H) |
| δ | 3.15 (mc) ppm | (2H) |
| δ | 3.75 (S) ppm | (3H) |
| δ | 4.30 (bS) ppm | (1H) |
| δ | 5.78 (d) ppm | (1H) |
| δ | 5.92 (d) ppm | (1H) |
| δ | 7.22 (t) ppm | (1H) |

Result of elementary analysis (as C$_8$H$_{12}$N$_2$O)

|  | C | H | N | O |
|---|---|---|---|---|
| Found (%) | 63.21 | 7.89 | 18.36 | 10.54 |
| Calculated (%) | 63.13 | 7.95 | 18.41 | 10.51 |

Molecular weight by GC-MS 152

EXAMPLE 6

In the same reacting apparatus as in Example 1, 20 g of 2-bromo-6-isopropylaminopyridine, 70 ml of methanol and 14 g of potassium hydroxide were charged and they were subjected to reacting each other at 160° C. for 4 hours. After completion of the reaction, the similar experimental procedure as in Example 3 was carried out to give 7.3 g of 2-methoxy-6-isopropylaminopyridine of b.p. 127°–128° C./20 mmHg.

Infrared absorption spectrum (NaCl) 3420 (—NH), 2960 (C—H), 1600, 1465, 1425

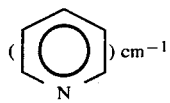

Nuclear magnetic resonance absorption spectrum (CDCl₃, internal standard TMS)

| δ | 1.20 (d) ppm | (6H) |
|---|---|---|
| δ | 3.85 (S) ppm | (3H) |
| δ | 3.90 (mc) ppm | (1H) |
| δ | 4.19 (bS) ppm | (1H) |
| δ | 5.84 (d) ppm | (1H) |
| δ | 5.98 (d) ppm | (1H) |
| δ | 7.28 (t) ppm | (1H) |

Result of elementary analysis (as $C_9H_{14}N_2O$)

|  | C | H | N | O |
|---|---|---|---|---|
| Found (%) | 65.11 | 8.43 | 9.57 | 16.89 |
| Calculated (%) | 65.03 | 8.49 | 9.63 | 16.85 |

Molecular weight by GC-MS 166

EXAMPLE 7

In the same reacting apparatus as in Example 1, 20 g of 2-chloro-6-methoxypyridine, 25 g of n-propylamine and 80 ml of water were charged and they were subjected to reacting each other at 180° C. for 5 hours. After completion of the reaction, the similar experimental procedure was carried out to give 9.3 g of 2-methoxy-n-propylaminopyridine of b.p. 90°–91° C./4 mmHg.

Infrared absorption spectrum (NaCl) 3420 (—NH), 2950 (C—H), 1600, 1460, 1420

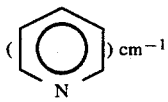

Nuclear magnetic reasonance absorption spectrum (CDCl₃, internal standard TMS)

| δ | 0.90 (t) ppm | (3H) |
|---|---|---|
| δ | 1.50 (mc) ppm | (2H) |
| δ | 3.08 (g) ppm | (2H) |
| δ | 3.75 (S) ppm | (3H) |
| δ | 4.50 (bS) ppm | (1H) |
| δ | 5.78 (d) ppm | (1H) |
| δ | 5.92 (d) ppm | (1H) |
| δ | 7.20 (t) ppm | (1H) |

Result of elementary analysis (as $C_9H_{12}N_2O$)

|  | C | H | N | O |
|---|---|---|---|---|
| Found (%) | 65.02 | 8.52 | 9.68 | 16.78 |
| Calculated (%) | 65.03 | 8.49 | 9.63 | 16.85 |

Molecular weight by GC-MS 166

Examples of compounds which were derived from the compounds of this invention and applications thereof as herbicide are described hereinbelow.

APPLICATION EXAMPLE 1

To the mixture of 1.38 g of 2-methoxy-6-methylaminopyridine, which is one of the compounds of this invention, and the same amount of anhydrous potassium carbonate in 20 ml of acetone, 2.23 g of O-2-chlorothioformate dissolved in 20 ml of acetone was added under stirring at room temperature. After 30 minutes, the reaction mixture was extracted with benzene, washed with water, dried and recrystallized to give 2.75 g of O-2-naphthyl N-(6-methoxy-2-pyridyl)-N-methylthiocarbamate.

m.p. 95.5°–97° C.

Elementary analysis (as $C_{18}H_{16}N_2O_2S$)

|  | C | H | N |
|---|---|---|---|
| Found (%) | 66.42 | 4.89 | 8.81 |
| Calculated (%) | 66.65 | 4.97 | 8.64 |

Paddy field soil was charged into porcelain pots having a diameter of 9 cm, and then water was added. After the soil was tilled, seeds of weeds were sown on the surface of the soil and two bunches of rice plants (variety: Nihonbare) being in 2-leaf stage were transplanted in 1 cm depth. The pots were flooded to give water depth of 2 cm on the next day, and water dispersible powder containing 10% of O-2-naphthyl N-(6-methoxy-2-pyridyl)-N-methylthiocarbamate, which was dispersed in 10 ml of water per pot, was added dropwise into every pots on the surface of water for treatment thereof. Then, they were settled in a greenhouse, and the herbicidal effects as well as the influence against the rice plants were examined after 3 weeks. As the result, it was harmless to the rice plants at all in applied amount of 125 g/10 a and effectively prevented barnyard grass, umbrella plant, bulrush, monochoria and rotala indica by 100%.

APPLICATION EXAMPLE 2

To the mixture of 1.52 g of 2-ethylamino-6-methoxypyridine and 1.38 g of anhydrous potassium carbonate in 20 ml of acetone, 2.15 g of O-4-isopropylphenyl chlorothioformate dissolved in 20 ml of acetone was added under stirring at room temperature. After 30 minutes stirring in this state, it was heated under reflux for 2 hours. After cooled to room temperature, the reaction mixture was poured into cold water, and the product was extracted with benzene.

The benzene solution was washed with water and saturated sodium chloride aqueous solution in this order, and benzene was distilled off under reduced pressure after dried over anhydrous magnesium sulfate. The residue was purified through column chromatography (silica gel, developed with benzene) to give 2.67 g (yield 81%) of O-4-isopropylphenyl N-ethyl-N-(6-methoxy-2-pyridyl)thiocarbamate. This compound was recrystallized from ethanol to give colorless crystal of m.p. 53°–54° C.

Elementary analysis (as $C_{18}H_{22}N_2O_2S$)

|  | C | H | N |
|---|---|---|---|
| Found (%) | 65.17 | 6.67 | 8.63 |
| Calculated (%) | 65.42 | 6.71 | 8.47 |

Paddy field soil was charged into porcelain pots having a diameter of 9 cm, and then water was added. After the soil was tilled, seeds of weeds were sown on the surface of the soil and two bunches of rice plants (variethy: Nihonbare) being 2-leaf stage were transplanted in 1 cm depth. On the next day, the pots were flooded to give water depth of 2 cm, and water dispersible powder containing 10% of O-4-isopropylphenyl N-ethyl-N-(6-methoxy-2-pyridyl)thiocarbamate, which was dispersed in 10 ml of water per pot, was added dropwise into every pots on the surface of water for treatment thereof. Then, they were settled in a greenhouse, and the herbicidal effects as well as the influence against the rice plants were examined after 3 weeks.

As the result, it was harmless at all in applied amount of 125 g/10 a and effectively prevented barnyard grass, umbrella plant and monochoria by 100%.

What is new and desired to be secured by Letters Patent of the United States is:

1. 2-alkylaminopyridine derivatives represented by the general formula

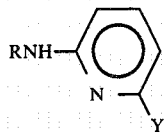

wherein R denotes a lower alkyl group of $C_1$ to $C_3$ and Y denotes a methoxy group.

2. The compound of claim 1 which is 2-methoxy-6-methylaminopyridine.

3. The compound of claim 1 which is 2-ethylamino-6-methoxypyridine.

4. The compound of claim 1 which is 2-methoxy-6-isopropylaminopyridine.

5. The compound of claim 1 which is 2-methoxy-6-n-propylaminopyridine.

* * * * *